United States Patent [19]

Patel et al.

[11] Patent Number: 5,591,726
[45] Date of Patent: Jan. 7, 1997

[54] HETEROCYCLYLALKYL DIARYLBORON ESTER AND THIOESTER FUNGICIDAL AGENTS

[75] Inventors: Bomi P. Patel, Bryn Mawr, Pa.; Henry Van Tuyl Cotter, Ingelheim, Germany; Jerome M. Lavanish, Yardley, Pa.

[73] Assignee: American Cyanamid Company, Madison, N.J.

[21] Appl. No.: 313,525

[22] Filed: Sep. 26, 1994

[51] Int. Cl.$^6$ .......................... A61K 31/69; A01N 55/08; C07F 5/02
[52] U.S. Cl. ................ 514/64; 544/229; 546/13; 548/110
[58] Field of Search .................. 514/64; 544/229; 546/13; 548/110

[56] References Cited

U.S. PATENT DOCUMENTS

| | | | |
|---|---|---|---|
| 3,211,679 | 10/1965 | updegraff | 106/18.3 |
| 3,717,655 | 2/1973 | Godefroi | 548/341.1 |
| 4,723,984 | 2/1988 | Holmwood et al. | 504/272 |
| 4,983,589 | 1/1991 | Tsang et al. | 514/64 |
| 5,348,947 | 9/1994 | Patel | 514/64 |

FOREIGN PATENT DOCUMENTS 1218623  1/1971  United Kingdom.

OTHER PUBLICATIONS

Farfán et al, *J. Chem. Soc. Perkin Trans.* 2, pp. 527–532 (1992).

*Primary Examiner*—Emily Bernhardt
*Attorney, Agent, or Firm*—John W. Hogan, Jr.

[57] ABSTRACT

The present invention provides heterocyclylalkyl diarylboron ester and thioester compounds of formula I

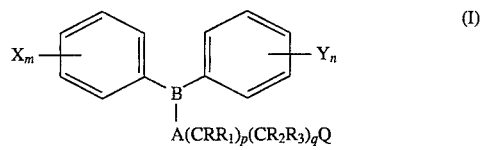

and their use for the prevention, control or amelioration of diseases caused by fungi. Further provided are compositions and methods comprising those compounds for the protection of plants from fungal infection and disease.

21 Claims, No Drawings

HETEROCYCLYLALKYL DIARYLBORON ESTER AND THIOESTER FUNGICIDAL AGENTS

BACKGROUND OF THE INVENTION

Phytopathogenic fungi are the causal agents for many diseases that infect and destroy crops. In particular, the diseases cereal powdery mildew, cereal septoria nodorum blotch, tomato/potato early blight, Cercospora leaf spots, apple scab, grape and other downy mildews, Botrytis diseases, rice blast and sheath blight are especially devastating.

In spite of the commercial fungicides available today, diseases caused by fungi still cause significant crop damage. Accordingly, there is ongoing research to create new and more effective fungicides for controlling or preventing diseases caused by phytopathogenic fungi.

It is an object of the present invention to provide compounds which are highly effective for controlling or preventing phytopathogenic fungal infections in agronomic crops, both growing and harvested.

It is also an object of the present invention to provide a method for the prevention, control or amelioration of a disease caused by a phytopathogenic fungus.

These and other objects of the present invention will become more apparent from the detailed description thereof set forth below.

SUMMARY OF THE INVENTION

The present invention describes heterocyclylalkyl diarylboron ester and thioester compounds and their use as fungicidal agents.

The heterocyclylalkyl diarylboron ester and thioester compounds of the present invention have the following structural formula I:

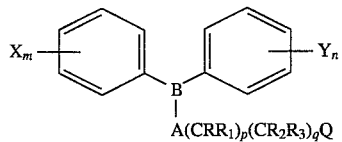

wherein

X and Y are each independently halogen, $C_1$–$C_6$alkoxy, $C_1$–$C_6$haloalkoxy, $C_1$–$C_6$alkyl or $C_1$–$C_6$haloalkyl;

m and n are each independently an integer of 0, 1, 2 or 3;

A is O or S;

p and q are each independently an integer of 0 or 1, provided that at least one of p and q is 1;

R, $R_1$, $R_2$ and $R_3$ are each independently hydrogen, $C_1$–$C_6$alkyl or phenyl optionally substituted with one or more halogen, $C_1$–$C_4$alkyl, $C_1$–$C_4$haloalkyl, $C_1$–$C_4$alkoxy, $C_1$–$C_4$haloalkoxy, cyano, nitro, $C(O)R_4$ or $NR_5R_6$ groups, and when R and $R_1$ or $R_2$ and $R_3$ are taken together with the carbon atom to which they are attached, they may form a 5- or 6-membered cycloalkyl ring optionally substituted with 1 to 3 $C_1$–$C_4$ alkyl, $C_1$–$C_4$ haloalkyl or $C_1$–$C_4$ alkoxy groups or when R or $R_1$ and $R_2$ or $R_3$ are taken together with the carbon atoms to which they are attached, they may form a 5- or 6-membered cycloalkyl ring optionally substituted with 1 to 3 $C_1$–$C_4$ alkyl, $C_1$–$C_4$ haloalkyl or $C_1$–$C_4$ alkoxy groups;

Q is W, $R_7$W, or

$R_7$ is $C_1$–$C_3$ alkyl optionally substituted with 1 to 3 of the following $C_1$–$C_6$alkyl optionally substituted with one phenyl group optionally substituted with one or more halogen, $C_1$–$C_4$alkyl, $C_1$–$C_4$haloalkyl, $C_1$–$C_4$alkoxy, $C_1$–$C_4$haloalkoxy, cyano, nitro, $C(O)R_4$ or $NR_5R_6$ groups, or phenyl optionally substituted with one or more halogen, $C_1$–$C_4$alkyl, $C_1$–$C_4$haloalkyl, $C_1$–$C_4$ alkoxy, $C_1$–$C_4$haloalkoxy, cyano, nitro, $C(O)R_4$ or $NR_5R_6$ groups;

W is

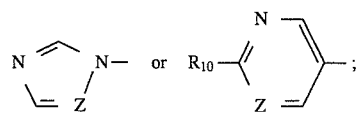

$R_8$ is hydrogen or $C_1$–$C_6$alkyl;

$R_9$ is $C_1$–$C_6$alkyl or phenyl optionally substituted with one or more halogen, $C_1$–$C_4$alkyl, $C_1$–$C_4$haloalkyl, $C_1$–$C_4$alkoxy, $C_1$–$C_4$haloalkoxy, cyano, nitro, $C(O)R_4$ or $NR_5R_6$ groups;

$R_4$, $R_5$, $R_6$ and $R_{10}$ are each independently hydrogen or $C_1$–$C_4$alkyl; and Z is CH or N;

or the optical isomers or diastereomers thereof.

This invention also relates to compositions and methods comprising those compounds for the prevention, control or amelioration of diseases caused by fungi.

DETAILED DESCRIPTION OF THE INVENTION

Phytopathogenic fungi are the causal agents for many diseases that infect and destroy agronomic crops, both growing and harvested. In the United States alone, agronomic crops must contend with several thousand species of fungi. Especially devastating are diseases such as cereal powdery mildew, cereal septoria nodorum blotch, tomato/potato early blight, Cercospora leaf spots, apple scab, grape and other downy mildews, Botrytis diseases, rice blast, sheath blight and the like. Accordingly, there is ongoing research to create new and more effective fungicides for preventing or controlling the vast array of fungal infections of crops.

Advantageously, the present invention provides a method for the prevention, control or amelioration of a disease caused by a fungus, preferably a phytopathogenic fungus, by contacting said fungus with a fungicidally effective amount of a formula I, heterocyclylalkyl diarylboron ester or thioester compound.

The present invention also provides a method for the protection of a plant, plant part, plant seed or tuber from fungal infection and disease by applying to the plant, plant part, plant seed or tuber, or to the medium or water in which it is growing, a fungicidally effective amount of a formula I, heterocyclylalkyl diarylboron ester or thioester compound.

The heterocyclylalkyl diarylboron ester and thioester compounds of the present invention have the following structural formula I:

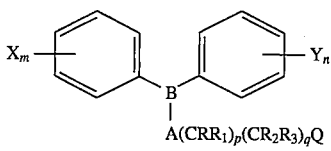

wherein

X and Y are each independently halogen, $C_1$–$C_6$alkoxy, $C_1$–$C_6$haloalkoxy, $C_1$–$C_6$alkyl or $C_1$–$C_6$haloalkyl;

m and n are each independently an integer of 0, 1, 2 or 3;

A is O or S;

p and q are each independently an integer of 0 or 1, provided that at least one of p and q is 1;

R, $R_1$, $R_2$ and $R_3$ are each independently hydrogen, $C_1$–$C_6$alkyl or phenyl optionally substituted with one or more halogen, $C_1$–$C_4$alkyl, $C_1$–$C_4$haloalkyl, $C_1$–$C_4$alkoxy, $C_1$–$C_4$haloalkoxy, cyano, nitro, $C(O)R_4$ or $NR_5R_6$ groups, and when R and $R_1$ or $R_2$ and $R_3$ are taken together with the carbon atom to which they are attached, they may form a 5- or 6-membered cycloalkyl ring optionally substituted with 1 to 3 $C_1$–$C_4$ alkyl, $C_1$–$C_4$ haloalkyl or $C_1$–$C_4$ alkoxy groups or when R or $R_1$ and $R_2$ or $R_3$ are taken together with the carbon atoms to which they are attached, they may form a 5- or 6-membered cycloalkyl ring optionally substituted with 1 to 3 $C_1$–$C_4$ alkyl, $C_1$–$C_4$ haloalkyl or $C_1$–$C_4$ alkoxy groups;

Q is W, $R_7$W, or

$R_7$ is $C_1$–$C_3$ alkyl optionally substituted with 1 to 3 of the following $C_1$–$C_6$alkyl optionally substituted with one phenyl group optionally substituted with one or more halogen, $C_1$–$C_4$alkyl, $C_1$–$C_4$haloalkyl, $C_1$–$C_4$alkoxy, $C_1$–$C_4$haloalkoxy, cyano, nitro, $C(O)R_4$ or $NR_5R_6$ groups, or phenyl optionally substituted with one or more halogen, $C_1$–$C_4$alkyl, $C_1$–$C_4$haloalkyl, C–$C_4$alkoxy, $C_1$–$C_4$haloalkoxy, cyano, nitro, $C(O)R_4$ or $NR_5R_6$ groups;

W is

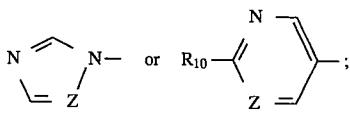

$R_8$ is hydrogen or $C_1$–$C_6$alkyl;

$R_9$ is $C_1$–$C_6$alkyl or phenyl optionally substituted with one or more halogen, $C_1$–$C_4$alkyl, $C_1$–$C_4$haloalkyl, $C_1$–$C_4$alkoxy, $C_1$–$C_4$haloalkoxy, cyano, nitro, $C(O)R_4$ or $NR_5R_6$ groups;

$R_4$, $R_5$, $R_6$ and $R_{10}$ are each independently hydrogen or $C_1$–$C_4$alkyl; and Z is CH or N;

or the optical isomers or diastereomers thereof.

Preferred fungicidal agents of the present invention are heterocyclylalkyl diarylboron ester compounds of formula I wherein X and Y are each independently halogen, $C_1$–$C_6$alkoxy, $C_1$–$C_6$haloalkoxy, $C_1$–$C_6$alkyl or $C_1$–$C_6$haloalkyl;

m and n are each independently an integer of 0, 1 or 2;

A is O;

p is 1;

q is 0;

R and $R_1$ are each independently hydrogen or phenyl optionally substituted with one or more halogen, $C_1$–$C_4$alkyl, $C_1$–$C_4$haloalkyl, $C_1$–$C_4$alkoxy or $C_1$–$C_4$haloalkoxy groups;

Q is w or $R_7$W;

$R_7$ is methyl optionally substituted with one or two of the following groups:

$C_1$–$C_6$alkyl optionally substituted with one phenyl group optionally substituted with one or more halogen, $C_1$–$C_4$alkyl, $C_1$–$C_4$haloalkyl, $C_1$–$C_4$alkoxy or $C_1$–$C_4$haloalkoxy groups, or phenyl optionally substituted with one or more halogen, $C_1$–$C_4$alkyl, $C_1$–$C_4$haloalkyl, $C_1$–$C_4$alkoxy or $C_1$–$C_4$haloalkoxy groups;

W is

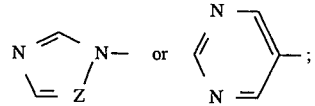

Z is CH or N.

Heterocyclylalkyl diarylboron ester compounds of the present invention which are particularly effective as fungicidal agents include (o-chlorophenyl) (p-chlorophenyl) (5-pyrimidinyl)methyl diphenylborinate;

1-tert-butyl-3-(p-chlorophenyl)-1-(1H-1, 2,4-triazol-1-yl-methyl)propyl diphenylborinate;

1-tert-butyl-3-(p-chlorophenyl)-1-(1H-1, 2,4-triazol-1-yl-methyl)propyl bis(p-fluorophenyl)borinate;

1-(2,4-dichlorophenyl)-2-(imidazol-1-yl)ethyl bis(p-fluorophenyl)borinate;

(o-chlorophenyl) (p-chlorophenyl) (5-pyrimidinyl)methyl bis(p-fluorophenyl)borinate; and 1-(2,4-dichlorophenyl)-2-(imidazol-1-yl)ethyl diphenylborinate, among others.

The term halogen used herein includes fluorine, chlorine, bromine and iodine. The terms "$C_1$–$C_4$haloalkyl", "$C_1$–$C_6$haloalkyl", "$C_1$–$C_4$haloalkoxy" and "$C_1$–$C_6$haloalkoxy" are defined as a $C_1$–$C_4$alkyl group, a $C_1$–$C_6$alkyl group, a $C_1$–$C_4$alkoxy group and a $C_1$–$C_6$alkoxy group each substituted with one or more halogen atoms, respectively. The term "medium" used herein is defined as any environment, including but not limited to artificial nutrients or soil, in which a plant can be kept, live or thrive.

The formula I compounds of the present invention are particularly useful in the prevention, control or amelioration of diseases such as wheat powdery mildew, wheat septoria nodorum blotch, tomato/potato early blight, sugar beet cercospora leaf spot, apple scab, grape downy mildew, rice blast and grape or pepper botrytis. Such diseases are caused by the phytopathogenic fungi *Erysiphe graminis f. sp. tritici, Septoria nodorum, Alternaria solani, Cercospora beticola, Venturia inaequalis, Plasmopara viticola, pyricularia grisea* and *Botrytis cinerea*, respectively.

Fungicidal heterocyclylalkyl diarylboron ester and thioester compounds of formula I may be prepared by reacting a substituted heterocyclic compound of formula II with a diarylborinic acid of formula III in the presence of an inert organic solvent such as ether, toluene, benzene and the like preferably with the azeotropic removal of water. The reaction scheme is shown below in Flow Diagram I.

Flow Diagram I

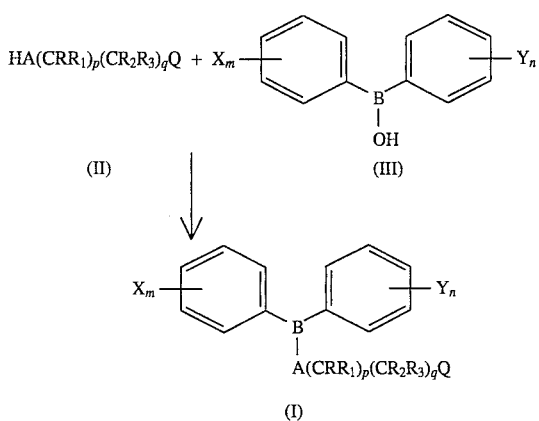

Surprisingly, it has been found that the compounds of the present invention are effective against fungi and the plant diseases they cause which are resistant to certain classes of fungicidal compounds such as inhibitors of the $\Delta^{14}$-demethylase enzyme in the ergosterol pathway.

Advantageously, the compounds of the present invention are particularly useful for controlling, preventing or ameliorating foliar cereal diseases such as Erysiphe and Septoria and top fruit diseases such as Venturia, Botrytis and Alternaria.

The heterocyclylalkyl diarylboron ester and thioester compounds of the present invention are also useful for the protection of growing or harvested plants from the damage caused by phytopathogenic fungal disease when applied to said plants at a fungicidally effective rate. The effective rate will vary depending upon factors such as the sensitivity of the target fungus, the environment of the treatment and other ambient conditions. In practice, generally about 10 ppm to about 1,000 ppm, preferably about 50 ppm to about 500 ppm of a formula I compound may be dispersed in an agronomically acceptable liquid or solid carrier and applied to the plant, plant part, seed or tuber, or to the medium or water in which the plant, plant part, seed or tuber is growing.

The fungicidal compounds of the invention may be formulated as concentrated solutions, emulsifiable concentrates, flowable concentrates, microemulsions and the like. Said compounds may also be formulated as dry compacted granules, granular compositions, dusts, dust concentrates, suspension concentrates, wettable powders, and the like. Those formulations which lend themselves to seed, tuber, medium, water and/or foliage applications to provide the requisite plant protection are suitable. Such formulations include the formula I compounds admixed with an agronomically acceptable inert solid or liquid carrier.

It is contemplated that the fungicidal compounds of the invention may be used in conjunction with, or in combination with, a pesticidally effective amount of one or more other pesticides, including but not limited to, anilazine, benalaxyl, benomyl, bitertanol, bordeaux mixture, carbendazim, carboxin, captafol, captan, chlorothalonil, cyproconazole, dichloran, diethofencarb, dimethomorph, diniconazole, dithianon, dodine, edifenphos, fenarimol, fenbuconazole, fenfuram, fenpropidin, fenpropimorph, fentin hydroxide, ferbam, flusilazole, flusulfamide, flutriafol, folpet, fosetyl, fuberidazole, guazatine, hexaconazole, imazalil, iprobenfos, iprodione, mancozeb, maneb, metalaxyl, metiram, myclobutanil, nuarimol, ofurace, oxadixyl, oxycarboxin, penconazole, probenazole, prochloraz, propiconazole, pyrazophos, tebuconazole, thiabendazole, thiophanate, thiophanate-methyl, triadimefon, triadimenol, triarimol, tricyclazole, tridemorph, triflumizole, triforine, vinclozolin, and/or zineb.

Where compositions of the invention are to be employed in combination treatments with other pesticidal agents, the composition may be applied concurrently as an admixture of the components as described above, or may be applied sequentially.

In order to facilitate a further understanding of the invention, the following examples are presented primarily for the purpose of illustrating more specific details therof. The invention should not be deemed limited thereby except as defined in the claims.

EXAMPLE 1

Preparation of 1-(2,4-Dichlorophenyl)-2-(imidazol-1-yl)ethyl bis(p-fluorophenyl)borinate

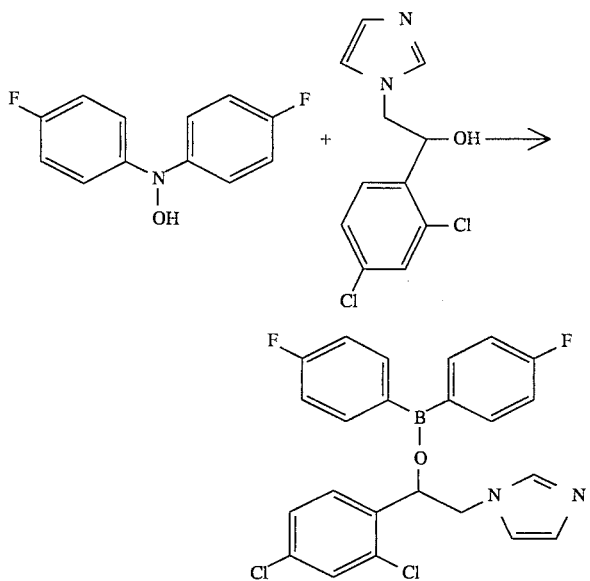

A mixture of β-(2,4-dichlorophenyl)imidazole-1-ethanol' (0.58 g, 2.26 mmol) in ether is added to a solution of bis(p-fluorophenyl)borinic acid (0.5 g, 2.29 mmol) in ether under nitrogen. The reaction mixture is refluxed overnight, cooled to and stirred at room temperature for six hours and filtered to obtain a solid. The solid is washed with hexanes and dried to give the title product as a white solid (1.02 g, mp 228°–232° C.).

Using essentially the same procedure, but substituting diphenylborinic acid for bis(p-fluorophenyl)borinic acid, 1-(2,4-dichlorophenyl)-2-(imidazol-1-yl)ethyl diphenylborinate is obtained as a white solid.

EXAMPLE 2

Preparation of 1-Tert-butyl-3-(p-chlorophenyl)-1-(1H-1,2,4-triazol-1-ylmethyl)propyl diphenylborinate

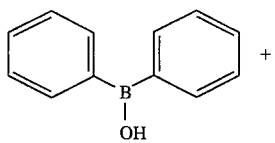

-continued

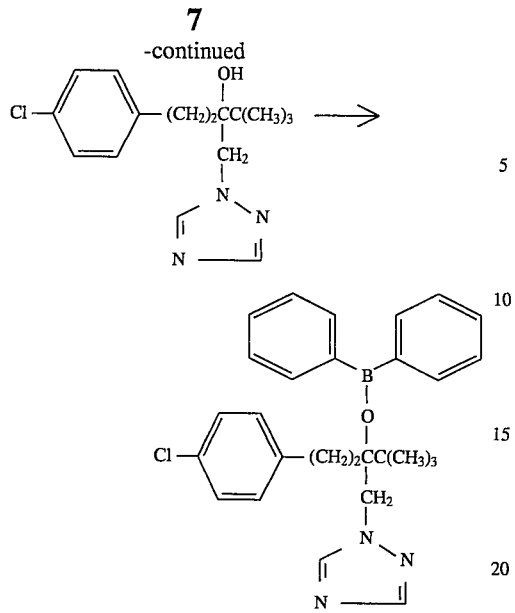

A solution of diphenylborinic acid (0.11 g, 0.60 mmol) in toluene is added to a solution of 1-(4-chlorophenyl)-4,4-dimethyl-3-(1H-1,2,4-triazol-1-ylmethyl)pentan-3-ol (0.21 g, 0.68 mmol) in a 1:1 ether/toluene solution. The reaction mixture is heated at reflux for 3 days with removal of water (Dean Stark), cooled and concentrated in vacuo to obtain a residue. The residue is chromatographed using silica gel and hexane/ethyl acetate solutions to give the title product as a pale yellow solid, mp 197° C.

Using essentially the same procedure, but using the appropriately substituted borinic acid and the appropriately substituted alcohol, the following compounds are obtained:

factant manufactured by Atlas Chemical Industries, to give a concentration of 200 ppm.

Host plants are sprayed with the test solution, dried and inoculated with fungi. When disease symptom development is optimal, the plants are rated for disease control according to the rating scale shown below. Each test contains inoculated treated plants, inoculated untreated plants and a reference standard. When more than one test is run, the data are averaged. The data obtained are shown in Table I.

Compounds employed in this in vivo fungicidal evaluation and in the in vitro fungicidal evaluation in the following example are given a compound number and identified by name. Data in Table I are reported by compound number.

| RATING SCALE | |
|---|---|
| Rating | Range % Disease Control |
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |

| X | Y | R | $R_1$ | $R_2$ | $R_3$ | q | W | mp °C |
|---|---|---|---|---|---|---|---|---|
| F | F | —C(CH$_3$)$_3$ | —CH$_2$CH$_2$—(4-Cl-phenyl) | H | H | 1 | —N(triazole) | 212 |
| F | F | (4-Cl-phenyl) | (2-Cl-phenyl) | | | 0 | (pyrazole) | 169 |
| H | H | (4-Cl-phenyl) | (2-Cl-phenyl) | | | 0 | (pyrazole) | 194 |

EXAMPLE 3

Evaluation of in vivo fungicidal activity of test compounds

Test compounds are dissolved or suspended in acetone and diluted with deionized water containing about 0.05% TWEEN®20, a polyoxyethylene sorbitan monolaurate sur-

PHYTOPATHOGENIC FUNGI

| Symbol | Disease | Pathogen |
|---|---|---|
| AS | Apple Scab | *Venturia inaequalis* |
| GDM | Grape Downy Mildew | *Plasmopara viticola* |
| PB | Pepper Botrytis | *Botrytis cinerea* |
| RB | Rice Blast | *Pyricularia grisea* |
| SBC | Sugar Beet Cercospora | *Cercospora beticola* |
| TEB | Tomato Early Blight | *Alternaria solani* |
| WPM | Wheat Powdery Mildew | *Erysiphe graminis* f. sp. tritici |
| WSN | Wheat Septoria Nodorum | *Septoria nodorum* |

COMPOUNDS EVALUATED AS FUNGICIDAL AGENTS

| Compound Number | |
|---|---|
| 1 | 1-(2,4-Dichlorophenyl)-2-(imidazol-1-yl)ethyl bis(p-fluorophenyl)borinate |
| 2 | (o-Chlorophenyl)(p-chlorophenyl)(5-pyrimidinyl)-methyl diphenylborinate |
| 3 | 1-Tert-butyl-3-(p-chlorophenyl)-1-(1H-1,2,4-triazol-1-ylmethyl)propyl diphenylborinate |
| 4 | 1-Tert-butyl-3-(p-chlorophenyl)-1-(1H-1,2,4-triazol-1-ylmethyl)propyl bis(p-fluorophenyl)borinate |
| 5 | (o-Chlorophenyl)(p-chlorophenyl)(5-pyrimidinyl)-methyl bis(p-fluorophenyl)borinate |
| 6 | 1-(2,4-Dichlorophenyl)-2-(imidazol-1-yl)ethyl diphenylborinate |

TABLE I

In Vivo Fungicidal Evaluations

| Compound Number | Rate (ppm) | AS | GDM | PB | RB | SBC | TEB | WPM | WSN |
|---|---|---|---|---|---|---|---|---|---|
| 1 | 200 | 0 | 0 | 0 | 8 | 6 | 4 | 8 | 0 |
| 2 | 200 | 9 | 3 | 8 | 0 | 9 | 8 | 8 | 8 |
| 3 | 200 | 8 | 9 | 6 | 6 | 6 | 6 | 8 | 0 |
| 4 | 200 | 7 | 8 | 7 | 6 | 6 | 6 | 8 | 2 |
| 5 | 200 | 7 | 0 | 0 | 0 | 7 | 3 | 8 | 7 |
| 6 | 200 | 3 | 0 | 0 | 0 | 5 | 0 | 8 | 0 |

EXAMPLE 4

Evaluation of in vitro funqicidal activity of test compounds

Test compounds are dissolved or suspended in acetone and dispersed into cell well plates containing a suspension of ground fungal mycelia/spores in a nutrient broth. Assay plates are incubated for 3–7 days at 21° C. Growth inhibition is measured visually and is rated using the following scale:

| Rating | % Growth Inhibition |
|---|---|
| 0 | 0 |
| 1 | 1–29 |
| 3 | 30–59 |
| 5 | 60–89 |
| 7 | 90–99 |
| 9 | 100 |

Untreated controls, solvent blanks and reference standards are included in each test.

Assay fungi include the plant pathogens, *Pythium ultimum* (PYTHUL); *Rhizoctonia solani* (RHIZSO); *Fusarium oxysporum f. sp. cucumerinum* (FUSOXC); and *Pseudocercosporella herpotrichoides* (PSDCHE).

When more than one test is run, the data are averaged. The data obtained are shown in Table II. The compounds evaluated are reported by compound number given in Example 3.

TABLE II

In Vitro Fungicidal Evaluations

| Compound Number | Rate (ppm) | FUSOXC | PYTHUL | RHIZSO | PSDCHE |
|---|---|---|---|---|---|
| 1 | 25 | 5 | 5 | 7 | 0 |
| 2 | 25 | 9 | 7 | 9 | 0 |
| 3 | 2S | 9 | 9 | 9 | 0 |
| 4 | 25 | 9 | 9 | 9 | 0 |
| 5 | 25 | 0 | 1 | 7 | 0 |
| 6 | 25 | 9 | 7 | 9 | 0 |

EXAMPLE 5

Evaluation of in vitro funqicidal activity of test compounds against sensitive and resistant fungus strains Two hundred microliters of fungal inoculum are added to individual wells on a 96-well microtiter plate [50,000 conidia/mL in potato dextrose broth for *Septoria nodorum* (propiconazole-resistant and -sensitive strains) and *Cladosporium cucumerinum* (fenarimol-resistant and -sensitive strains), and 250,000 sporidia/mL in potato dextrose broth for *Ustilago avenae* (triadimefon-resistant and -sensitive strains)]. Test compounds are dissolved or suspended in N,N-dimethylformamide and dispersed into individual wells. The wells are shaken and initial OD 550 readings (optical density reading at 550 nm) are taken. The wells are incubated in a humidified chamber at 21° C. or room temperature for 50 to 54 hours. During the incubation period, wells containing *Ustilago avenae* are shaken continuously and wells containing *Septoria nodorum* or *Cladosporium cucumerinum* are not shaken. After the incubation period, OD 550 readings are taken again and fungal growth is estimated by the difference between the OD 550 readings. Concentrations of test compounds that cause 50% growth reductions ($EC_{50}$'s) are calculated from the fungal growth data. Resistance factors are then calculated by dividing the $EC_{50}$'s for the resistant strains by the $EC_{50}$'s for the sensitive strains. A resistance factor of 1.0 indicates that the assay fungus resistant strain is not cross-resistant to the corresponding test compound. A resistance factor greater than 1.0 indicates that the assay fungus resistant strain is cross-resistant to the corresponding test compound.

The resistance factors for the test compounds are shown in Table III.

As can be seen from the data in Table III, the assay fungus resistant strains are significantly less resistant to the compounds of the present invention when compared to fenarimol, tebuconazole and miconazole nitrate.

TABLE III

|  | Resistance Factor | | |
| --- | --- | --- | --- |
|  | *Septoria nodorum* | *Ustilago avenae* | *Cladosporium cucumerinum* |
| Test Compound | | | |
| (o-Chlorophenyl)(p-chlorophenyl)(5-pyrimidinyl)-methyl diphenylborinate | 1.3 | 1.3 | — |
| 1-Tert-butyl-3-(p-chlorophenyl)-1-(1H-1,2,4-triazol-1-ylmethyl)propyl diphenylborinate | 1.8 | 2.0 | 1.7 |
| 1-Tert-butyl-3-(p-chlorophenyl)-1-(1H-1,2,4-triazol-1-ylmethyl)propyl bis(p-fluorophenyl)-borinate | 1.9 | 2.3 | 1.3 |
| 1-(2,4-Dichlorophenyl)-2-(imidazol-1-yl)ethyl bis(p-fluorophenyl)borinate | 1.2 | 2.6 | 1.5 |
| 1-(2,4-Dichlorophenyl)-2-(imidazol-1-yl)ethyl diphenylborinate | 1.0 | 1.6 | 1.1 |
| Comparative Compound | | | |
| Fenarimol | 9.6 | 9.9 | — |
| Tebuconazole | 6.1 | — | — |
| Econazole nitrate | 1.8 | 2.0 | 2.0 |
| Miconazole nitrate | 2.5 | 4.1 | 2.4 |

— = no evaluation

What is claimed is:

1. A compound having the structural formula

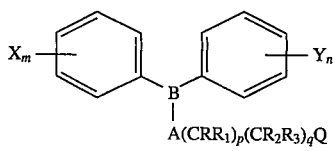

wherein

X and Y are each independently halogen, $C_1$–$C_6$alkoxy, $C_1$–$C_6$haloalkoxy, $C_1$–$C_6$alkyl or $C_1$–$C_6$haloalkyl;

m and n are each independently an integer of 0, 1, 2 or 3;

A is O or S;

p and q are each independently an integer of 0 or 1, provided that at least one of p and q is 1;

R, $R_1$, $R_2$ and $R_3$ are each independently hydrogen,
   phenyl optionally substituted with one or more halogen, $C_1$–$C_4$alkyl, $C_1$–$C_4$haloalkyl, $C_1$–$C_4$alkoxy, $C_1$–$C_4$haloalkoxy, cyano nitro $C(O)R_4$ or $NR_5R_6$ groups, or
   when R and $R_1$ or $R_2$ and $R_3$ are taken together with the carbon atom to which they are attached, they may form a 5- or 6-membered cycloalkyl ring optionally substituted with one to three $C_1$–$C_4$alkyl, $C_1$–$C_4$haloalkyl or $C_1$–$C_4$alkoxy groups, or
   when R or $R_1$ and $R_2$ or $R_3$ are taken together with the carbon atoms to which they are attached, they may form a 5- or 6-membered cycloalkyl ring optionally substituted with one to three $C_1$–$C_4$alkyl, $C_1$–$C_4$haloalkyl or $C_1$–$C_4$alkoxy groups;

Q is

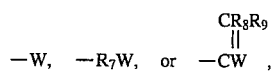

$R_7$ is $C_1$–$C_3$alkyl optionally substituted with one to three of the following
   $C_1$–$C_6$alkyl optionally substituted with one phenyl group optionally substituted with one or more halogen, $C_1$–$C_4$alkyl, $C_1$–$C_4$haloalkyl, $C_1$–$C_4$alkoxy, $C_1$–$C_4$haloalkoxy, cyano, nitro, $C(O)R_4$ or $NR_5R_6$ groups, or
   phenyl optionally substituted with one or more halogen, $C_1$–$C_4$alkyl, $C_1$–$C_4$haloalkyl, $C_1$–$C_4$alkoxy, $C_1$–$C_4$haloalkoxy, cyano, nitro, $C(O)R_4$ or $NR_5R_6$ groups;

W is

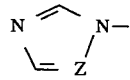

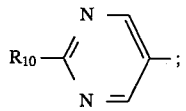

$R_8$ is hydrogen or $C_1$–$C_6$alkyl;

$R_9$ is $C_1$–$C_6$alkyl or phenyl optionally substituted with one or more halogen, $C_1$–$C_4$alkyl, $C_1$–$C_4$haloalkyl, $C_1$–$C_4$alkoxy, $C_1$–$C_4$haloalkoxy, cyano, nitro, $C(O)R_4$ or $NR_5R_6$ groups;

$R_4$, $R_5$, $R_6$ and $R_{10}$ are each independently hydrogen or $C_1$–$C_4$alkyl; and Z is CH or N;

or the optical isomers or diastereomers thereof.

2. The compound according to claim 1 wherein m and n are each independently an integer of 0, 1 or 2;

A is O;

p is 1;

q is 0 or 1;

R and $R_1$ are each independently hydrogen,
  phenyl optionally substituted with one or more halogen, $C_1-C_4$alkyl, $C_1-C_4$haloalkyl, $C_1-C_4$alkoxy or $C_1-C_4$haloalkoxy groups;

$R_2$ and $R_3$ are hydrogen;

Q is -W; and

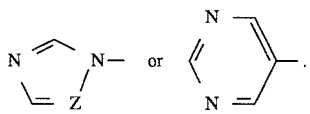

3. The compound according to claim 2 wherein m and n are each independently an integer of 0 or 1;

X and Y are F;

R is hydrogen, $C_1-C_4$alkyl or
  phenyl substituted with one chlorine atom; and $R_1$ is $C_1-C_3$alkyl or
  phenyl substituted with one or two chlorine atoms.

4. The compound according to claim 3 which is (o-chlorophenyl)(p-chlorophenyl)(5-pyrimidinyl)methyl diphenylborinate.

5. The compound according to claim 3 which is 1-tert-butyl-3-(p-chlorophenyl)-1-(1H-1,2,4-triazol-1-ylmethyl)propyl diphenylborinate.

6. The compound according to claim 3 which is 1-tert-butyl-3-(p-chlorophenyl)-1-(1H-1, 2,4-triazol-1-ylmethyl)propyl bis(p-fluorophenyl)borinate.

7. The compound according to claim 3 which is 1-(2,4-dichlorophenyl)-2-(imidazol-1-yl)ethyl bis(p-fluorophenyl)borinate.

8. The compound according to claim 3 which is (o-chlorophenyl) (p-chlorophenyl) (5-pyrimidinyl)methyl bis (p-fluorophenyl)borinate.

9. The compound according to claim 3 which is 1-(2,4-dichlorophenyl)-2-(imidazol-1-yl)ethyl diphenylborinate.

10. A method for the prevention, control or amelioration of a disease caused by a phytopathogenic which comprises contacting said fungus with a fungicidally effective amount of a compound having the structural formula

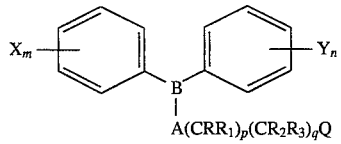

wherein X, Y, A, R, $R_1$, $R_2$, $R_3$, Q, p, q, m and n are as described in claim 1.

11. The method according to claim 9 wherein m and n are each independently an integer of 0, 1 or 2;

A is O;

p is 1;

q is 0 or 1;

R and $R_1$ are each independently hydrogen,
  phenyl optionally substituted with one or more halogen, $C_1C_4$alkyl, $C_1-C_4$haloalkyl, $C_1-C_4$alkoxy or $C_1-C_4$haloalkoxy groups;

$R_2$ and $R_3$ are hydrogen;

Q is -W;

W is

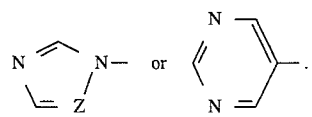

12. The method according to claim 11 wherein m and n are each independently an integer of 0 or 1;

X and Y are F;

R is hydrogen, $C_1-C_4$alkyl or
  phenyl substituted with one chlorine atom; and $R_1$ is $C_1-C_3$alkyl or
  phenyl substituted with one or two chlorine atoms.

13. The method according to claim 12 wherein the compound is selected from the group consisting of (o-chlorophenyl) (p-chlorophenyl) (5-pyrimidinyl)methyl diphenylborinate; 1-(2,4-dichlorophenyl)-2-(imidazol-1-yl)ethyl bis(p-fluorophenyl)borinate;

(o-chlorophenyl) (p-chlorophenyl) (5-pyrimidinyl)methyl bis(p-fluorophenyl)borinate; and 1-(2,4-dichlorophenyl)-2-(imidazol-1-yl)ethyl diphenylborinate.

14. The method according to claim 10 wherein the compound is applied at a concentration of about 10 ppm to 1,000 ppm.

15. A method for the protection of a plant, plant seed or tuber from fungal infection and disease which comprises applying to the plant, plant part, plant seed or tuber, or to the soil or water in which it is growing, a fungicidally effective amount of a compound having the structural formula

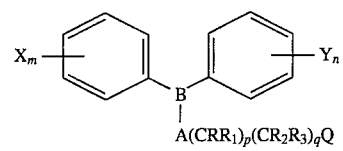

wherein X, Y, A, R, $R_1$, $R_2$, $R_3$, Q, p, q, m and n are as described in claim 1.

16. The method according to claim 15 wherein m and n are each independently an integer of 0, 1 or 2;

A is O;

p is 1;

q is 0 or 1;

R and $R_1$ are each independently hydrogen,
  phenyl optionally substituted with one or more halogen, $C_1-C_4$alkyl, $C_1-C_4$haloalkyl, $C_1-C_4$alkoxy or $C_1C_4$haloalkoxy groups;

$R_2$ and $R_3$ are hydrogen;

Q is -W; and

W is

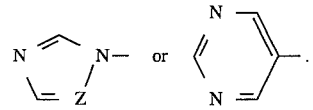

17. The method according to claim 16 wherein m and n are each independently an integer of 0 or 1;

X and Y are F;

R is hydrogen, $C_1-C_4$alkyl or
  phenyl substituted with one chlorine atom; and $R_1$ is $C_1-C_3$alkyl or phenyl substituted with one or two chlorine atoms.

18. The method according to claim 17 wherein the compound is selected from the group consisting of (o-chlorophenyl) (p-chlorophenyl) (5-pyrimidinyl)methyl diphenylborinate;

1-(2,4-dichlorophenyl)-2-(imidazol-1-yl)ethyl bis (p-fluorophenyl)borinate;

(o-chlorophenyl) (p-chlorophenyl) (5-pyrimidinyl)methyl bis(p-fluorophenyl)borinate; and 1-(2,4-dichlorophenyl)-2-(imidazol-1-yl)ethyl diphenylborinate.

19. The method according to claim 15 wherein the compound is applied to the plant at a rate of about 0.015 kg/ha to about 3.0 kg/ha.

20. A composition for controlling phytopathogenic fungi which comprises an agronomically acceptable carrier and a fungicidally effective amount of a compound having the structural formula

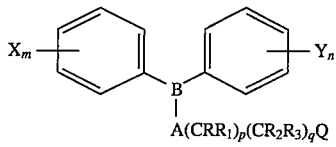

wherein X, Y, A, R, $R_1$, $R_2$, $R_3$, Q, p, q, m and n are as described in claim 1.

21. The composition according to claim 20 wherein m and n are each independently an integer of 0, 1 or 2;

A is O;

p is 1;

q is 0 or 1;

R and $R_1$ are each independently hydrogen, phenyl optionally substituted with one or more halogen, $C_1$-$C_4$alkyl, $C_1$-$C_4$haloalkyl, $C_1$-$C_4$alkoxy or $C_1$-$C_4$haloalkoxy groups;

$R_2$ and $R_3$ are hydrogen;

Q is -W; and

W is

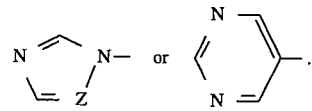

* * * * *